（12）United States Patent
Ortmaier et al.

(10) Patent No.: US 8,392,022 B2
(45) Date of Patent: Mar. 5, 2013

(54) DEVICE COMPRISING A ROBOT, MEDICAL WORK STATION, AND METHOD FOR REGISTERING AN OBJECT

(75) Inventors: Tobias Ortmaier, Hemmingen (DE); Dirk Jacob, Augsburg (DE); Thomas Neff, Munich (DE)

(73) Assignee: KUKA Laboratories GmbH, Augsburg (DE)

( * ) Notice: Subject to any disclaimer, the term of this patent is extended or adjusted under 35 U.S.C. 154(b) by 330 days.

(21) Appl. No.: 12/743,264

(22) PCT Filed: Nov. 18, 2008

(86) PCT No.: PCT/EP2008/065753
§ 371 (c)(1),
(2), (4) Date: May 17, 2010

(87) PCT Pub. No.: WO2009/065827
PCT Pub. Date: May 28, 2009

(65) Prior Publication Data
US 2010/0274389 A1 Oct. 28, 2010

(30) Foreign Application Priority Data
Nov. 19, 2007 (DE) .......................... 10 2007 055 203

(51) Int. Cl.
*G05B 15/00* (2006.01)

(52) U.S. Cl. ........................................ 700/258; 700/259

(58) Field of Classification Search .................. 700/258, 700/259
See application file for complete search history.

(56) References Cited

U.S. PATENT DOCUMENTS

| 5,868,675 | A | 2/1999 | Henrion et al. |
| 6,228,089 | B1 | 5/2001 | Wahrburg |
| 6,895,268 | B1 | 5/2005 | Rahn et al. |
| 2004/0077939 | A1 | 4/2004 | Graumann |
| 2007/0078473 | A1 | 4/2007 | Bodduluri et al. |

FOREIGN PATENT DOCUMENTS

| DE | 102 49 786 A1 | 5/2004 |
| WO | 2007/003949 A1 | 1/2007 |
| WO | 2008/058520 A2 | 5/2008 |

OTHER PUBLICATIONS

European Patent Office; International Search Report in International Patent Application No. PCT/EP2008/065753 dated Mar. 24, 2009; 6 pages.

*Primary Examiner* — Eric Culbreth
(74) *Attorney, Agent, or Firm* — Wood, Herron & Evans, LLP

(57) ABSTRACT

The invention relates to a medical device, a medical work station, and a method for registering an object (P). The medical device comprises a navigation system (17, 18) and a robot (R) having several axes of rotation (1-6). The navigation system (17, 18) comprises a detection device (18) for detecting prominent points on an object (P) or markers (M) placed on the object (P) as well as a processing device (17) for determining the position of the object (P) on the basis of the prominent points or markers (M) detected by means of the detection device (18). The detection device (18) of the navigation system is mounted on the robot (R).

14 Claims, 4 Drawing Sheets

Figure 1:
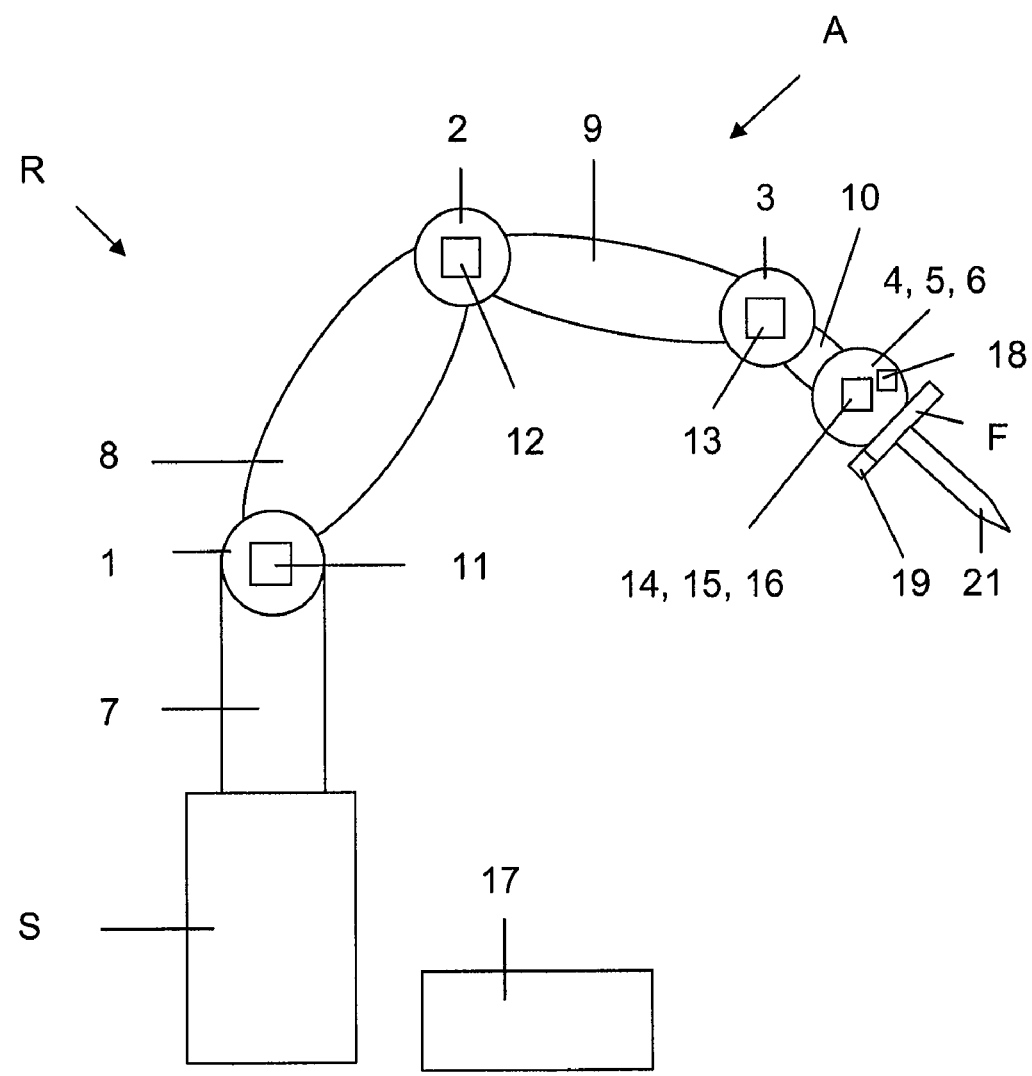

DEVICE COMPRISING A ROBOT, MEDICAL WORK STATION, AND METHOD FOR REGISTERING AN OBJECT

The invention relates to a device comprising a robot, to a medical work station, and to a method for registering an object.

U.S. 2004/0077939 A1 discloses a medical work station with an X-ray apparatus, a surgical instrument, a position detecting system and a robot guiding the surgical instrument for treating a patient in an at least partially automated manner. In order to detect the positions of the surgical instrument, the X-ray apparatus and the patient, position markers are arranged on the X-ray apparatus, on the patient, and on the surgical instrument or on the robot, which are registered by an optical position detection apparatus of the position detection system. Based on an evaluation of the images of the position markers recorded with the optical position detection apparatus, it is possible to determine the position, and possibly also the orientation of the position markers, and thus of the surgical instrument, of the X-ray apparatus and of the patient in space.

U.S. Pat. No. 6,228,089 B1 discloses a device for positioning and guiding a surgical tool in orthopedic interventions, which has an industrial robot with a program-controlled, multi-jointed robot arm including a mounting plate and a manually guidable sensor apparatus attached to the mounting plate, for three-dimensional object surveying in the tool coordinate system of the industrial robot. The sensor apparatus comprises a manually guidable multi-jointed feeler arm with sensors for detecting the joint positions or a measuring arrangement with remote data transmission which has a stationary receiver, a tracing stylus with a transmitter and a transmitter attached to the mounting plate. The transmitter comprises a plurality of signal generators in a rigidly prescribed spatial correlation, which emit locating signals that are picked up by the receiver.

The object of the invention is to create prerequisite conditions for a medical work station with a robot, so that positions of the robot and at least one other object can be determined more precisely.

An additional object of the invention is to specify a device having a robot for a correspondingly configured medical work station.

The problem of the invention is solved by a device having a navigation system that has a detection device for detecting distinctive sites of an object or markers positioned on the object and a processing device for determining the position of the object on the basis of the distinctive sites or markers detected with the detection device, and
a robot with a plurality of axes of rotation, to which the detection device of the navigation system is attached.

Although the device according to the invention or the robot according to the invention is intended in particular for the medical environment, non-medical applications are also conceivable, for example in the servicing, inspection and repairing of machines.

If the object is a living being, then the problem of the invention is also solved by a medical technology work station having the device according to the invention and a patient-transport trolley that is intended for the living being to lie on it as the object.

Navigation systems are generally known in medical technology, in particular in minimally invasive medical technology, for example from U.S. Pat. No. 6,895,268 B1. Navigation systems include the detection device, which may have for example an optical detection device, in particular a camera, a laser tracking system, projectors for structured light or linear projectors. The detection device is set up in a generally known manner to detect the markers or distinctive sites of the surface of the object that are positioned on the object, in particular on the surface of the object. On the basis of the device for detecting the markers or distinctive sites, a computing device of the navigation system is able, in an essentially generally known manner, to determine the position of the living being and possibly its orientation. According to the invention, the detection device of the navigation system is attached to the robot. Due to the attachment of the detection device to the robot, the positions of the coordinate systems of the navigation system and the robot relative to each other are known, for which reason the navigation system does not need to determine the position and possibly the orientation of the robot by means of markers or distinctive sites of the robot. That results in prerequisite conditions so that the position of the object, in particular in relation to the robot, can be determined more precisely.

The detection device can be for example an integral component of the robot. That makes it possible to determine the position of the detection system relative to the robot, for example relative to a coordinate system of the robot, for example when manufacturing the robot. This position is preserved when the robot is in operation.

However, the detection device may also be attached to the robot rigidly but removably.

According to a variant of the medical technology device according to the invention, the detection device is an integral component of a robot arm of the robot, or is rigidly but removably attached thereto.

Robots in general are manipulating machines, which are equipped with useful tools for automatic handling of objects, and are programmable in a plurality of motion axes, in particular with regard to orientation, position and process sequence. Robots generally include the robot arm, which is also referred to as a manipulator, a control apparatus and possibly an effector, which may be designed for example as a gripper for gripping a tool, for example when used in medical technology, to grip a medical instrument, in particular a surgical instrument. The medical instrument may also be attached to the effector through an adapter, however. The manipulator or robot arm represents essentially the movable part of the robot. The robot arm has in particular a plurality of axes, which are driven for example by means of electric drives, by the control apparatus designed as a computer.

According to one embodiment of the medical technology device according to the invention, its robot has a lighting system attached to the robot. The lighting system is for example attached to the robot arm of the robot or integrated into it.

Because of the detection device of the navigation system attached to the robot, in particular to its robot arm, prerequisite conditions exist for example for improved accessibility of the detection system in particular in the area of operations, since the position of the detection system can be modified by a movement of the robot and thus adapted to conditions in the area of operations. If the device according to the invention, or the medical work station according to the invention, is used for a navigating operation, then the robot can for example automatically select a relatively favorable, in particular an optimal viewing angle for the detection device, so that the latter is able to register the markers or distinctive sites relatively well. The optional lighting system can also be carried along accordingly.

If the robot has redundant degrees of freedom, then it is also possible to change the viewing angle of the detection device while at the same time preserving the so-called tool center point (TCP). This is particularly advantageous when a medical instrument, in particular a surgical instrument, is attached to the robot. The medical, in particular surgical instrument may be used for example for an automatic operation on the object specified as a living being, by means of the robot.

According to one embodiment of the device according to the invention, its robot is set up so as to register the markers or distinctive sites of the object automatically. This results, according to another aspect of the present invention, in a method for registering an object, that has the following procedural step: automatic registration of distinctive sites of an object or of markers positioned on the surface of the object, by means of a robot to which a detection device of a navigation system for detecting the distinctive sites or the markers positioned on the object is attached, where the navigation system has a processing device for determining the position of the object on the basis of the distinctive sites or markers detected with the detection device.

In order to determine the position of the object, the navigation system determines the positions of the markers or distinctive sites. In order to be able to accomplish this, it may be necessary to register the markers or distinctive sites. According to one embodiment of the medical technology device according to the invention, this is accomplished by having its robot set up to register the markers or distinctive sites by seeking. According to another embodiment of the device according to the invention, its robot is set up so as to register the markers or distinctive sites by recording. The recording of the markers or distinctive sites may be done in particular by the detection device of the navigation system.

If, according to another embodiment of the medical technology device according to the invention, its robot is set up to detect a movement of the object and to update the positions of the markers or distinctive sites automatically on the basis of the detected movement, this results in prerequisite conditions for improved determination of the position of the object.

According to another variant of the device according to the invention, its robot is set up to re-register the markers or distinctive sites and/or to redetermine their positions automatically after certain time intervals, for example periodically.

It may thus be possible by means of the device according to the invention, to automatically register the object, in particular the living being as the object, with the help of the detection device attached to the robot. For example, algorithms for assessing the quality of the data detected by means of the detection device may also be utilized. This makes it possible to reduce the cost, and possibly the error quota, of manual registration. It also may be possible, when a change in location occurs due to a movement of the object or living being, to perform a re-registration relatively simply, which may be carried out for example one time on the basis of a certain procedure, or which may occur periodically and is thus able to correct possible position changes automatically.

Because of the attachment of the detection device to the robot, which can also be guided by hand, a variety of modes of registration are possible. Possibilities thus include manual registration by moving manually to defined points, i.e., distinctive sites or markers located on the object at the point of intervention; semiautomatic registration, in which defined points are moved to manually and the sections between them are detected automatically or scanned; and fully automatic registration, in which the entire registration process is carried out without manual intervention.

The device according to the invention can also work in cooperation with a plurality of robots, in which case in particular the positions of the additional robot arms are known.

The image data obtained by means of the detection device can also be combined for example with pre-operatively obtained picture data records which were recorded in particular from the object by means of a medical technical imaging device. Some examples of suitable medical technical imaging devices, which are able in particular to create three-dimensional picture data records of the object, include magnetic resonance devices, computer tomography devices, X-ray devices or ultrasound devices. Alternatively or in addition, data from a CAD system may also be used. That makes it possible to enhance these picture data records with the additionally obtained data recorded by means of the detection device, whereby the work of a surgeon, for example, can be facilitated accordingly.

Figure 2:
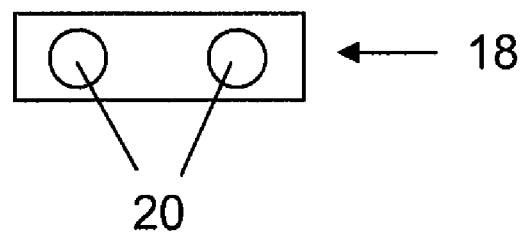
Figure 4:
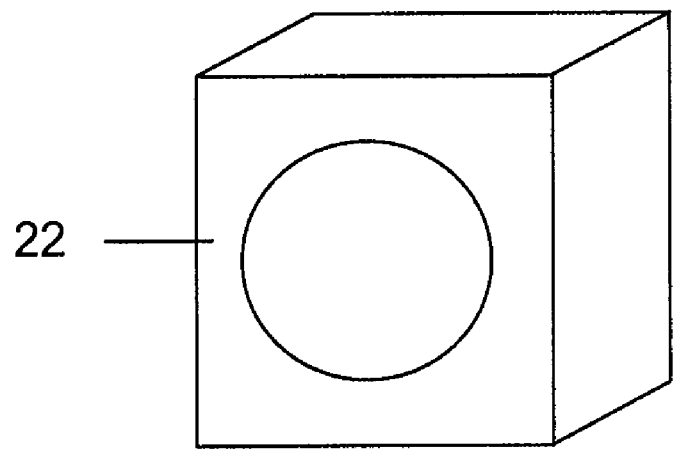
Figure 3:
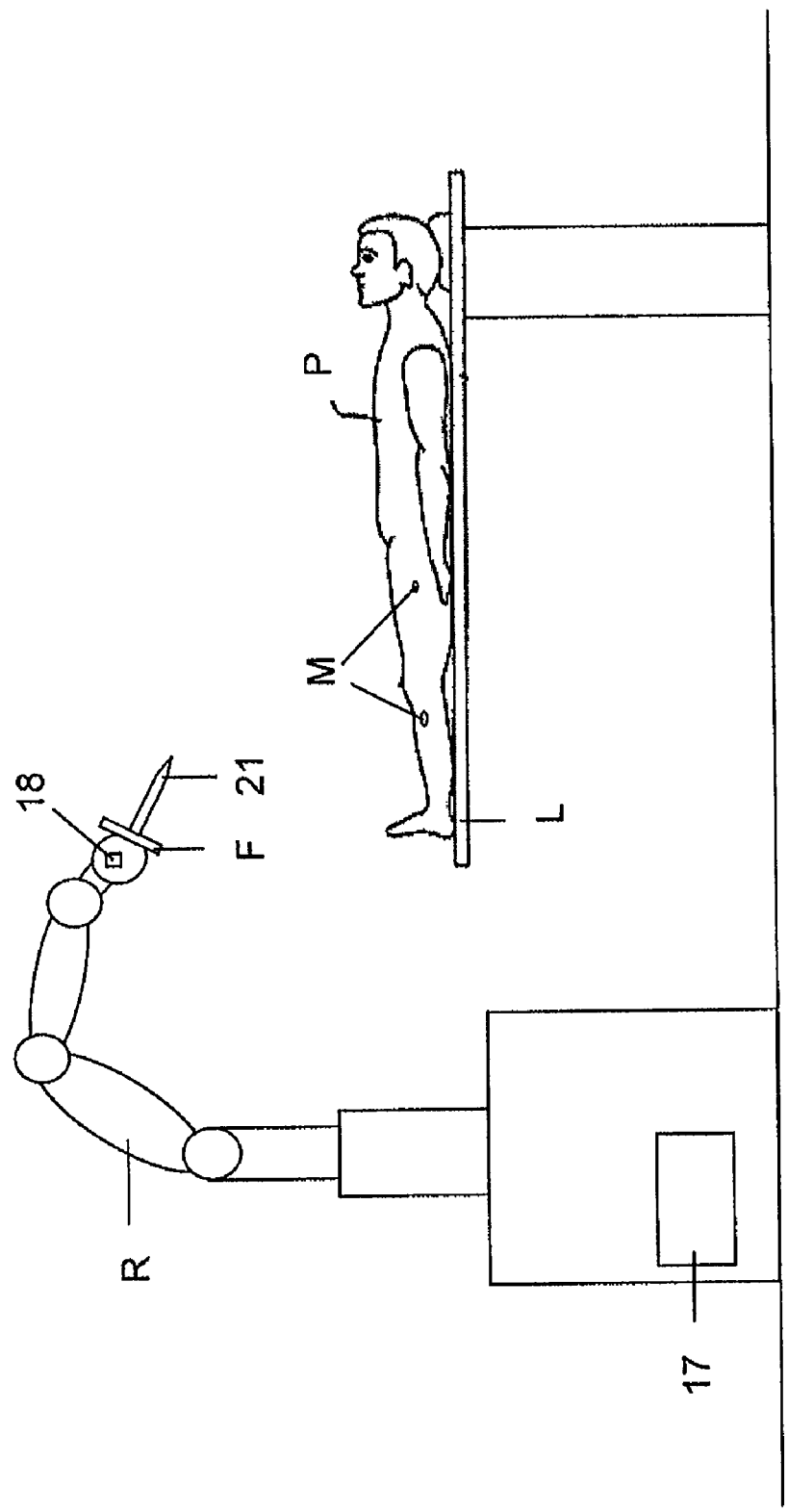
Figure 5:
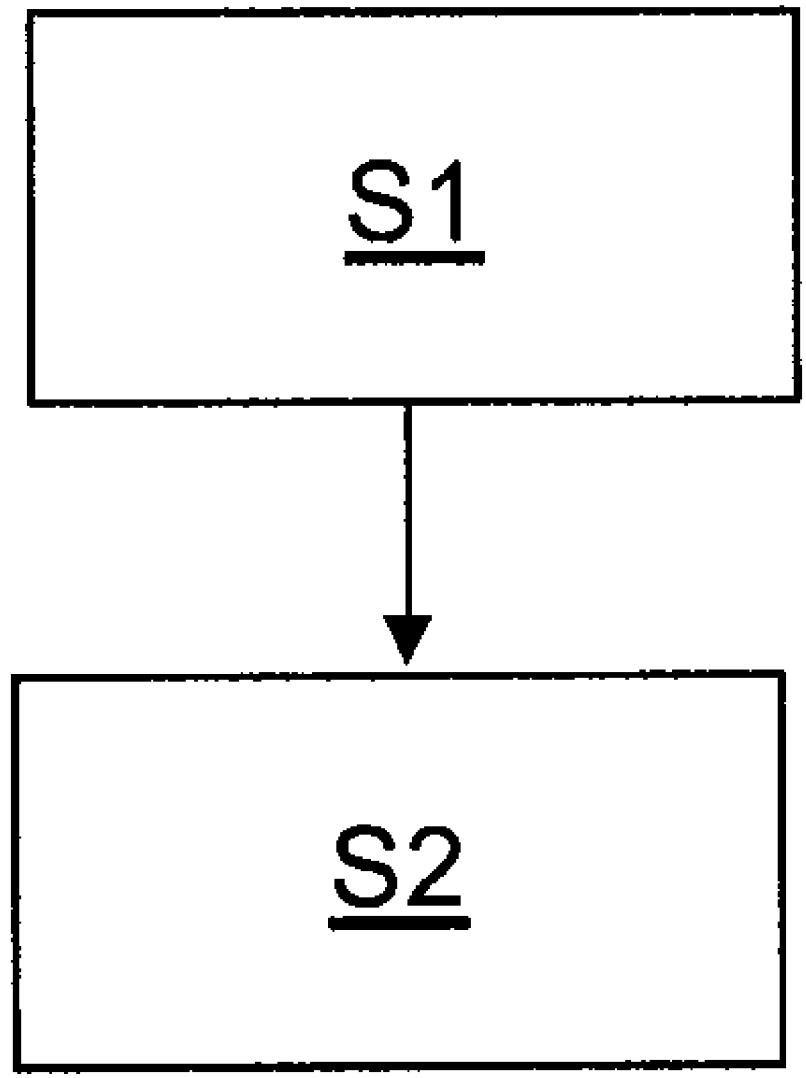

An example of an exemplary embodiment of the invention is depicted in the attached schematic drawings. The figures show the following:

FIG. 1 a robot,
FIG. 2 a detection device of a navigation system,
FIG. 3 a medical work station
FIG. 4 a medical technical imaging device, and
FIG. 5 a flow chart to illustrate a registration process.

FIG. 1 shows a robot R having a robot arm A, which in the case of the present exemplary embodiment is attached to a base S. Robot arm A represents essentially the movable part of robot R, and includes a plurality of axes 1-6, a plurality of levers 7-10 and a flange F, to which for example in the case of the present exemplary embodiment a surgical instrument is attached through an adapter, which is not shown in further detail. Surgical instrument 21 is for example an endoscope.

In the case of the present exemplary embodiment, each of the axes 1-6 is moved with an electric drive 11-16, which are electrically connected in a non-depicted manner to a control computer 17 of robot R, so that control computer 17 or a computer program running on control computer 17 is able to actuate electric drives 11-16 in such a way that the position and orientation of flange F of robot R can be set essentially freely in space. Electric drives 11-16 of robot R each include for example an electric motor and possibly power electronics that actuate the motors.

In the case of the present exemplary embodiment, robot R further comprises a detection device 18 of a navigation system, depicted in greater detail in FIG. 2. Navigation systems as such are known to the person skilled in the art, for example from U.S. Pat. No. 6,895,268 B1, and are provided for determining the position of an object, for example a living being or a medical instrument.

Navigation systems may be for example magnetic or optical navigation systems, and are utilized for example to determine the position and possibly the orientation of an object, for example a patient P lying on a patient-transport trolley in FIG. 3.

In order to determine the position of the patient, markers M for example are placed on the latter or on his or her surface, whose positions are determined by the navigation system. The situation of the markers, i.e., their positions and orientations relative to patient P, must therefore be known, and are determined in a generally known manner.

In the case of the present exemplary embodiment, detection device 18 has a stereo camera 20 which takes pictures of the markers M. In the case of the present exemplary embodiment, detection device 18 or its stereo camera 20 is connected in a manner not shown with control computer 17 of robot R, on which a computer program is running that analyzes the pictures of the markers M of patient P taken by stereo camera 20 in a generally known manner and on the basis of the analysis, and determines the positions of the markers M and hence the position of patient P in space.

In the case of the present exemplary embodiment, detection device 18 is integrated with its stereo camera 20 into robot arm A. Because of this integration, the position of detection device 18 in space is known, as a result of which the position of patient P in space can also be calculated.

In the case of the present exemplary embodiment, provision is made for robot R to treat patient P with medical instrument 21 in an automatic manner. An appropriate computer program for this treatment is also running on control computer 17. Based on the position and orientation of medical instrument 21, which are determinable on the basis of the position and orientation of robot R or on the basis of the position of detection device 18 relative to robot R, and the position and possibly orientation of patient P determined by means of detection device 18, it is possible for robot R to move medical instrument 21 in a previously specified manner in such a way that patient P is treated as desired.

In order to obtain the position and possibly the orientation of patient P in space, it is necessary in the case of the present exemplary embodiment to first register the markers M. FIG. 5 illustrates the method employed in the case of the present exemplary embodiment to register the markers M.

In the process of the registration, the starting situation or starting position of patient P in space relative to the operation situs and to patient-transport trolley L is detected. To that end, in the case of the present exemplary embodiment the markers M are scanned automatically by means of stereo camera 20, step S1 of the flow chart in FIG. 5.

In the case of the present exemplary embodiment, provision is also made so that control computer 17 or a computer program running on control computer 17 detects a movement of patient P on the basis of the recorded markers M. The movement is detected for example by analyzing the pictures taken with stereo camera 20.

If patient P moves to a greater degree than specified, then in the case of the present exemplary embodiment robot R automatically updates the position and/or orientation of patient P, step S2 of the flow chart.

Alternatively or in addition, there can also be provision for the registration of patient P and/or the determination of the patient's position and/or orientation to be repeated at predetermined time intervals, in particular periodically.

In the case of the present exemplary embodiment, there is also a lighting system 19 mounted on flange F, which illuminates in particular the area of medical instrument 21.

In the case of the present exemplary embodiment, there is also provision for combining image data obtained with the help of stereo camera 20 with a picture data record of patient P, in particular three-dimensional, created prior to the operation. The pre-operatively obtained picture data record, in particular three-dimensional, was produced for example by means of a medical technical imaging device 22 depicted in FIG. 4, for example a magnetic resonance device, a computer tomography device, an X-ray device or an ultrasound device.

In the case of the present exemplary embodiment, detection device 18 of the navigation system is integrated into robot arm A. Detection device 18 may also be integrated into a stationary part of robot R, for example its base S, or may also be attached rigidly but removably to robot R, in particular to its robot arm A.

Instead of markers M on patient P, distinctive sites on patient P may also be used for detecting the patient's position and possibly orientation.

The invention claimed is:

1. A robotic apparatus for treating an object, comprising:
a navigation system including a detection device configured to detect a plurality of distinctive sites of an object or a plurality of markers associated with the object, and a processing device communicating with the detection device and configured to determine a position and an orientation of the object based on the plurality of distinctive sites or the plurality of markers detected by the detection device; and
a robot having at least one arm and a plurality of axes of rotation for the arm, the detection device being coupled to the robot;
wherein the robot is configured to automatically register the plurality of markers or the plurality of distinctive sites associated with the object; and
wherein the robot is configured to automatically re-register, at predetermined time intervals, the plurality of markers or a position and orientation of the plurality of distinctive sites associated with the object.

2. A robotic apparatus for treating an object, comprising:
a navigation system including a detection device configured to detect a plurality of distinctive sites of an object or a plurality of markers associated with the object, and a processing device communicating with the detection device and configured to determine a position and an orientation of the object based on the plurality of distinctive sites or the plurality of markers detected by the detection device; and
a robot having at least one arm and a plurality of axes of rotation for the arm, the detection device being coupled to the robot;
wherein the robot is configured to automatically register the plurality of markers or the plurality of distinctive sites associated with the object by moving toward the markers or toward the distinctive sites, respectively, or by recording the position and orientation of the plurality of markers or the plurality of distinctive sites.

3. The robotic apparatus of claim 2, wherein the detection device is an optical device selected from the group consisting of a camera, a laser tracking system, a plurality of projectors for structured light, and a plurality of linear projectors.

4. The robotic apparatus of claim 2, wherein the detection device is integral with the robot arm.

5. The robotic apparatus of claim 2, wherein the detection device is removably coupled to the robot arm.

6. The robotic apparatus of claim 2, wherein the robot includes a lighting system.

7. The robotic apparatus of claim 2, wherein the robot is configured to detect a movement of the object and, in response to the detection, update the respective positions and orientations of the plurality of markers or the respective positions of the plurality of distinctive sites.

8. The robotic apparatus of claim 2, further comprising:
a surgical instrument coupled to the robot.

9. The robotic apparatus of claim 2, further comprising:
a patient transport trolley accessible by the robot and configured to permit a living being to lie thereon.

10. A method for registering a position and orientation of an object with a robot having a detection device, the method comprising:
using the robot to automatically detect a plurality of distinctive sites or a plurality of markers associated with the object;
using a processing device to determine a position and orientation of the object based on the detection of the plurality of distinctive sites or the plurality of markers;

automatically registering the plurality of distinctive sites or the plurality of markers; and automatically seeking the plurality of distinctive sites or the plurality of markers prior to registration thereof.

11. The method of claim 10, wherein registering the position and orientation of the object includes registering respective positions and orientations of the detected plurality of distinctive sites or the detected plurality of markers, the method further comprising:

automatically detecting movement of the object; and automatically updating, based on the detected movement of the object, the registered respective positions and orientations of the plurality of distinctive sites or the detected plurality of markers.

12. The method of claim 10, further comprising:

automatically re-registering the respective positions and orientations of the plurality of distinctive sites or the respective plurality of markers at predetermined time intervals.

13. The method of claim 10, wherein registering the position and orientation of the object includes automatically recording the plurality of distinctive sites or the plurality of markers.

14. The method of claim 10, wherein detecting the plurality of distinctive sites or the plurality of markers comprises using one of a camera, a laser tracking system, a plurality of projectors for structured light, or a plurality of linear projectors.

* * * * *